United States Patent [19]

Krespan

[11] 4,335,255
[45] Jun. 15, 1982

[54] ALKYL PERFLUORO (2-METHYL-5-OXO-3-OXAHEXANOATE)

[75] Inventor: Carl G. Krespan, Wilmington, Del.

[73] Assignee: E. I. Du Pont de Nemours and Company, Wilmington, Del.

[21] Appl. No.: 136,991

[22] Filed: Apr. 3, 1980

[51] Int. Cl.³ .................. C07C 69/708; C07C 69/716; C07C 121/34
[52] U.S. Cl. .................................. 560/174; 526/244; 526/245; 526/247; 260/465.6; 260/544 F; 260/544 L; 560/183; 560/184; 562/577; 562/586; 568/674; 564/203
[58] Field of Search .......................................... 560/174

[56] References Cited

U.S. PATENT DOCUMENTS

| | | | |
|---|---|---|---|
| 3,114,778 | 12/1963 | Fritz et al. | 526/247 |
| 3,250,808 | 5/1966 | Moore et al. | 260/535 |
| 3,274,239 | 9/1966 | Selman | 260/514 |
| 3,310,606 | 3/1967 | Fritz | 526/276 |
| 3,321,517 | 5/1967 | Selman | 260/544 |
| 3,367,960 | 2/1968 | Sweeney et al. | 560/174 |
| 3,449,371 | 6/1969 | Throckmorton | 560/174 X |
| 3,450,716 | 6/1969 | Selman | 260/340.2 |
| 3,847,978 | 11/1974 | Sianesi et al. | 260/535 H |
| 4,116,888 | 9/1978 | Ukihashi et al. | 521/31 |
| 4,131,740 | 12/1978 | England | 560/174 |
| 4,140,699 | 2/1979 | Martini | 260/33.2 R |
| 4,176,215 | 11/1979 | Molnar et al. | 521/27 |
| 4,275,225 | 6/1981 | Krespan | 560/174 |

FOREIGN PATENT DOCUMENTS 1817826 12/1971 Fed. Rep. of Germany .
52-84196 7/1977 Japan .
52-120983 10/1977 Japan .

OTHER PUBLICATIONS

Fluorine Chemistry Reviews, vol. 5, edited by P. Tarrant, Marcel Dekker, Inc., New York, N.Y. (1971) pp. 85–113.

Primary Examiner—Joseph Paul Brust

[57] ABSTRACT

Ketoester of the formula

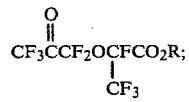

α-carboxylate-ω-acyl fluoride of the formula

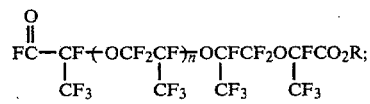

vinyl ether of the formula

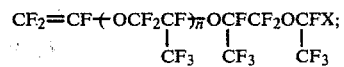

divinyl ether of the formula

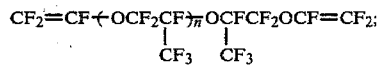

allyl ether of the formula

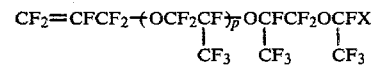

and film-forming copolymers, useful as molding resins, of the vinyl ether and/or the divinyl ether or the allyl ether and a fluorinated vinyl monomer, for example, tetrafluoroethylene, wherein, in the above formulas, n is 0 to 6, p is 0 to 7; X is $CO_2M$, $CO_2R$, $CO_2H$, $CONH_2$, COF, COCl or CN, M is alkali metal, ammonium or quaternary ammonium and R is $C_{1-8}$ alkyl, selected copolymers, after hydrolysis, being water-wettable and dyeable, exhibiting ion-exchange properties and being useful in curable fluoroelastomer compositions and, in film form, as the membrane in a chloroalkali electrolysis cell.

15 Claims, No Drawings

ALKYL PERFLUORO (2-METHYL-5-OXO-3-OXAHEXANOATE)

DESCRIPTION

Technical Field

This invention relates to alkyl perfluoro(2-methyl-5-oxo-3-oxohexanoates) and derivatives thereof, including copolymers of certain derivatives.

BACKGROUND

U.S. Pat. No. 3,321,517 discloses the preparation of the lactone perfluoro(3,6-dimethyl-2-oxo-1,4-dioxane), its hydrolysis to perfluoro(2-methyl-5-oxo-3-oxahexanoic)acid hydrate and the reaction of the hydrate with concentrated sulfuric acid to produce perfluoro(2-methyl-5-oxo-3-oxahexanoic)acid. No esters are disclosed.

U.S. Pat. No. 3,847,978 includes within its disclosure acids and esters of the formula

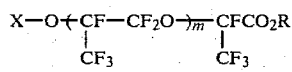

wherein R is H or alkyl, X is CF$_3$COCF$_2$,

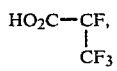

RO$_2$CCF$_2$ or

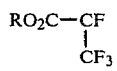

and m is an integer within the range 1–50. A similar disclosure appears in the related German Offenlegungschrift 1,817,826.

Japanese Kokai J52/120,983 discloses fluorocarbon copolymers having side chains which contain the moiety

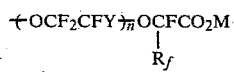

wherein R$_f$ is perfluoroalkyl of 1–5 carbon atoms, Y is F or R$_f$; n is 0–3 and M is H, NH$_4$ or a metal cation; also disclosed are cation exchange membranes of the copolymers.

U.S. Pat. No. 4,131,740 discloses alpha carboxylate-ω-vinyl ethers of the formula

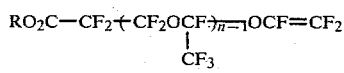

wherein R is alkyl of 1–6 carbon atoms and n is 1–6 and their preparation by pyrolysis of the corresponding acyl fluorides in the presence of Na$_2$CO$_3$ or Na$_3$PO$_4$; copolymers of the vinyl ethers and perfluorinated vinyl monomers such as tetrafluoroethylene are also disclosed.

U.S. Pat. No. 3,310,606 discloses perfluorinated divinyl ethers of the formula CF$_2$=CFO(CF$_2$)$_n$OCF=CF$_2$, wherein n is 2–24, their preparation by pyrolysis of the corresponding diacyl fluorides, and copolymers thereof with perfluorinated vinyl monomers.

South African Pat. No. 77/7158 discloses polyfluoroallyloxy compounds of the formula CF$_2$=CFCF$_2$OCF$_2$D wherein D can be linear or branched perfluoroalkyl of 1–10 carbon atoms, interruptable no more frequently than every second carbon atom by 1–4 ether oxygen atoms and having 0–2 functional groups. Although such disclosure embraces compounds of the formula

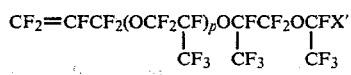

wherein X' is SO$_2$F, COF, CO$_2$H, Cl, OCF$_2$CF=CF$_2$, OCF$_2$CO$_2$R or CO$_2$R wherein R is CH$_3$ or C$_2$H$_5$, and p is 0–2, no method of preparing such compounds is provided.

U.S. Pat. No. 3,274,239 discloses fluorocarbon ethers which include those of the formula

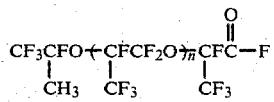

wherein n is an integer within the range 0–20, their preparation by the fluoride ion-catalyzed reaction of hexafluoropropene oxide and a perfluoroketone, and their pyrolysis to vinyl ethers.

DISCLOSURE OF INVENTION

For further comprehension of the invention, and of the objects and advantages thereof, reference may be made to the following description and to the appended claims in which the various novel features of the invention are made particularly set forth.

This invention provides the alkyl perfluoro(2-methyl-5-oxo-3-oxahexanote) having the formula

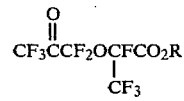

wherein R is alkyl of 1 to 8 carbon atoms, preferably 1 to 4 carbon atoms; the α-carboxylate-ω-acyl fluoride adduct of 1 with hexafluoropropene oxide (HFPO), that is, hexafluoroepoxypropane, the adduct having the formula

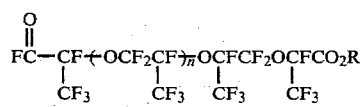

wherein R is defined as above and n is 0 to 6; the vinyl ether derived from 2 and having the formula

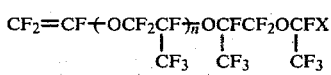

wherein X is CO$_2$M, CO$_2$R, CO$_2$H, COF, COCl, CONH$_2$ or CN, M is alkali metal, ammoium or quaternary ammonium and R and n are defined as above; the divinyl ether derived from 2 and having the formula

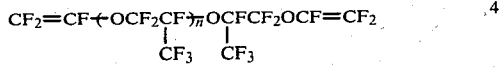

wherein n is defined as above; the allyl ether having the formula

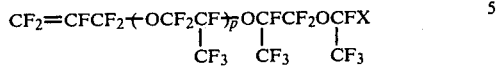

wherein p is 0–7 and X is defined as above; and copolymers of the vinyl ethers 3 and/or 4 or the allyl ether 5 and one or more fluorinated vinyl monomers selected from tetrafluoroethylene, trifluoroethylene, chlorotrifluoroethylene, vinylidene fluoride and, provided tetrafluoroethylene is also present, hexafluoropropene and a perfluoro(alkyl vinyl ether) wherein the alkyl group preferably is of 1 to 8 carbon atoms.

This invention also provides a process for preparing the ketoester of formula 1 from the known cyclic compounds perfluoro(3,6-dimethyl-2-oxo-1,4-dioxane), 6, 2-oxo-6-hydroxyperfluoro(3,6-dimethyl-1,4-dioxane), 7, or the lactone 2-oxo-6-alkoxyperfluoro(3,6-dimethyl-1,4-dioxane), 8, or contacting and reacting 6, 7 or 8 with an excess of an alkanol of 1 to 8 carbon atoms, optionally in the presence of an alkali metal fluoride when 6 is the starting compound or a mineral acid when 7 or 8 is the starting compound, to form an acyclic hemiketal, 9, and then reacting the hemiketal with P₂O₅, for example,

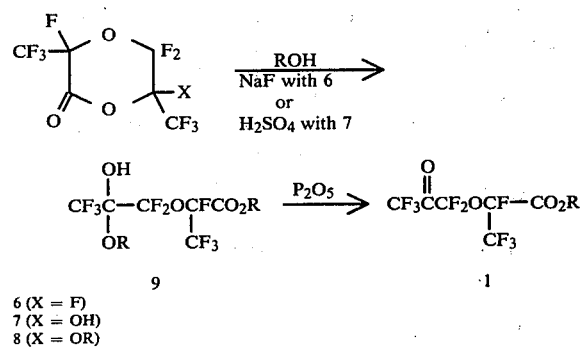

6 (X = F)
7 (X = OH)
8 (X = OR)

In this equation, although X and R are defined as above, it is to be understood that, in compound 9, the two R groups can be the same or different when 8 is the starting material, depending on the R selected in 8 and the R selected in ROH.

Reaction of 6 or 7 with an alkanol to form the hemiketal 9 requires a molar excess of alkanol with respect to 6 or 7. The molar ratio of alkanol to 6 or 7 generally is about 2:1 to 50:1, a ratio of 3:1 to 8:1 is preferred with the lactone 6, and a ratio of 12:1 to 40:1 is preferred with the lactol 7. A modest excess of alkanol is sufficient with the lactone 8. Thus, the molar ratio of alkanol to 8 can be slightly greater than 1:1. Although the alkanol can contain 1 to 8 carbon atoms, it preferably has 1 to 4 carbon atoms. Most preferably, the alcohol is methanol.

Reaction of the lactone 6 with the alkanol is optionally carried out in the presence of an approximately equimolar amount, with respect to the lactone, of an alkali metal fluoride, preferably sodium fluoride. The alkali metal fluoride serves to remove the hydrogen fluoride formed in the reaction. Reaction of the lactol 7 with an alkanol is enhanced by the presence of a catalytic amount of a strong acid such as sulfuric acid or a sulfonic acid; normally, about 0.005 to about 0.05 mol of acid per mol of lactol 7 is sufficient. A catalyst is not needed for the reaction of lactone 8 with an alkanol.

To produce the hemiketal 9, compound 6, 7 or 8 can be reacted with the alkanol at a temperature within the range 15°–150° C., preferably 20°–50° C. The reaction pressure can vary from about 0.1 atmosphere (10.1 kPa) to, for example, about 20 atmospheres (about 2000 kPa); atmospheric pressure (101 kPa) is preferred. A solvent can be present during the reaction. Suitable solvents include inert liquids such as diethylether, 1,1,2-trichloro-1,2,2-trifluoroethane and toluene; preferably, an excess of the alkanol, which also serves to increase reaction rate, is used as the solvent.

The hemiketal 9 can be converted to the ketoester 1 by contacting it with about 1 to 5 moles of P₂O₅ per mol of hemiketal at a temperature of 15°–100° C., preferably 20°–40° C. The product 1 is recovered from the reaction mixture by distillation under reduced pressure.

The lactol 7 can be prepared from the lactone 6 by hydrolysis in an excess of water at elevated tempeature. The acyclic intermediate, believed to have the structure $$HO_2C-\underset{\underset{CF_3}{|}}{\overset{\overset{OH}{|}}{C}}FOCF_2\underset{\underset{OH}{|}}{\overset{\overset{OH}{|}}{C}}-CF_3,$$

which is formed is reacted with P₂O₅, in the manner described above, to form 7.

The lactone 8 can be prepared from 6 or 7 by reaction thereof with an approximately equimolar amount of an alkanol of 1 to 8 carbon atoms; the reaction temperature, pressure and suitable solvents are as described above for preparing the hexiketal 9. Normally, the ketoester 1 is also formed as a coproduct. When larger amounts of alkanol are employed, the lactone 8 which is formed is converted to the hemiketal 9 to an extent which is dependent on such factors as the quantity of alkanol used, the reaction time and temperature and pressure.

The aforesaid adduct of formula b 2 is produced by reacting the fluorinated ketoester of formula 1 with HFPO in the presence of fluoride ion, the reaction occurring almost exclusively at the keto carbonyl group.

Fluorinated lactones such as 6 will also react with HFPO/F⁻ but almost exclusively at the ester carbonyl group to form HFPO adducts wherein the lactone ring is preserved, as described in U.S. Pat. No. 4,140,699.

The reaction of the fluorinated ketoester of formula 1 with HFPO can be carried out in an inert solvent such glyme (ethylene glycol dimethyl ether), diglyme (diethylene glycol dimethyl ether), tetrahydrofuran or acetonitrile, at about −20° to 100° C., preferably about 0° to 60° C., under a pressure of about 0.1 atmosphere (10.1 kPa) to, for example, 20 atmospheres (about 2000 kPa). Fluoride ion catalyst can be provided by a fluoride salt of an alkali metal, preferably cesium or potassium, or by an ammonium or quaternary ammonium fluoride.

The α-carboxylate-ω-acyl fluoride 2 of this invention can be converted to the fluorinated vinyl ether 3 wherein X is CO₂R and the divinyl ether 4 by pyrolysis at elevated temperature, normally about 200°–300° C., in the presence of an alkali metal basic salt such as Na$_2$CO$_3$ or Na$_3$PO$_4$ as described in the aforesaid U.S. Pat. No. 4,131,740; pressure can vary widely, but 1 atmosphere (101 kPa) or less is preferred. Formation of the monovinyl ether is favored by comparatively mild reaction conditions, for example, a temperature of 200°–260° C. in the presence of sodium phosphate; more rigorous conditions, for example, 260°–280° C. in the presence of sodium carbonate, favors formation of the divinyl ether.

The fluorinated ketoester of formula 1 or the α-carboxylate-ω-acyl fluoride 2 can be reacted with a perfluoroallylic compond such as perfluoroallyl fluorosulfate, -chloride or -bromide using procedures described in the aforesaid South African Patent No. 77/7158 to provide carboxyl-functional perfluoroallyl ether monomers

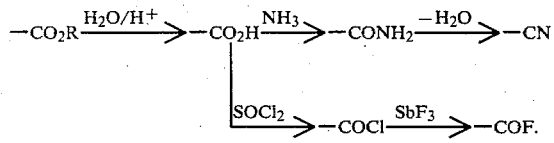

wherein R and p are defined as above.

The vinyl ether 3 and allyl ether 5, wherein X is CO$_2$R, can be converted by known methods into the corresponding carboxylic acids, acyl chlorides, acyl fluorides, amides and nitriles wherein X is CO$_2$H, COCl, COF, CONH$_2$ and CN, respectively. Two such methods can be represented by the equations

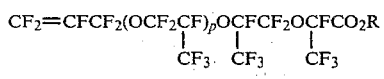

Alkaline hydrolysis of the aforesaid ester, acid or acyl halides results in the formation of CO$_2$M groups wherein M is alkali metal, ammonium or quaternary ammonium.

The fluorinated ethers 3, 4 and 5 are monomers which can be copolymerized with a fluorinated vinyl monomer such as tetrafluoroethylene, trifluoroethylene, chlorotrifluoroethylene, vinylidene fluoride, or combinations of these monomers; hexafluoropropene or a perfluoro(alkyl vinyl eyther) can be also copolymerized with ethers 3 and/or 4, or 5, provided tetrafluoroethylene is present as a comonomer. Tetrafluoroethylene is a preferred comonomer. Copolymerization can be initiated by a free radical generator such as a perfluoroacyl peroxide and is normally carried out in an inert aprotic medium such as 1,1,2-trichloro-1,2,2-trifluoroethane. The resultant copolymers are useful as molding resins. In addition, nitrile-functional copolymers provide cure sites for fluoroelastomer compositions. Copolymers which contain the functions —CO$_2$R, —CO$_2$H, —COCl or —COF can be hydrolyzed to water-wettable, dyeable compositions. Alkaline hydrolysis of the copolymers produces copolymers having ion-exchange properties, and films of the hydrolyzed copolymers are useful as membranes in chloroalkali electrolysis cells.

In the following examples of specific embodiments of the present invention, parts and percentages are by weight and temperatures are in ° Celsius, unless otherwise specified.

EXAMPLE 1

Methyl Perfluoro(2-methyl-5-oxo-3-oxohexanoate)
From the Lactone
Perfluoro(3,6-dimethyl-2-oxo-1,4-Dioxane)

A suspension of 50.4 g (1.2 mol) of NaF in 128 g (4.0 mol) of methanol was stirred and cooled with an ice bath while 310 g (1.0 mol) of perfluoro(3,6-dimethyl-2-oxo-1,4-dioxane) was added at a rate sufficient to maintain a temperature of 25°–30° C. The ice bath was removed after completion of the addition and the reaction mixture was stirred overnight. The NaF.HF was filtered off, the filter cake was rinsed well with ether, and the filtrates were added to 213 g (1.5 mol) of P$_2$O$_5$. The resultant mixture was allowed to stand for about 65 h and then distilled to give 272.6 g (85%) of methyl perfluoro(2-methyl-5-oxo-3-oxohexanoate), bp 48°–51° (50 mm), identified by IR and NMR.

EXAMPLE 2

A.
2-Oxo-6-hydroxyperfluoro(3,6-dimethyl-1,4-Dioxane)

Perfluoro(2-oxo-3,6-dimethyl-1,4-dioxane), 314 g (1.01 mol), was added dropwise to a slurry of 56.1 g (1.0 mol) of calcium oxide in 500 ml of water while the slurry was stirred in an ice bath. The resultant mixture was stirred for one hour, heated nearly to reflux for 30 min, and stirred for about 65 h. Upon evaporation of the water, the crystalline residue which remained was treated portionwise with 450 g (3.2 mol) of P$_2$O$_5$. The resultant mixture was heated slowly (exothermic reaction) to 150° and then distilled to give 246 g of crude 2-oxo-6-hydroxyperfluoro(3,6-dimethyl-1,4-dioxane), bp 70°–75° (50 mm); upon redistillation from a small amount of P$_2$O$_5$ 208 g (67%) of purified lactol was recovered, bp 71°–73° (50 mm). IR: 2.90 (free OH), 5.51 (fluorolactone C=O), 7.5–10μ (C—F, C—O). NMR: $^{19}$F −82.7 (several m, 7, CF$_3$+part of AB for O—CF$_2$) −113.0 and −115.6 ppm (m, 1 CF).

B. methyl Perfluoro(2-methyl-5-oxo-3-oxahexanoate)

A solution of 179 g (0.58 mol) of the lactol from Part A and 1 ml of conc H$_2$SO$_4$ in 500 ml of methanol was refluxed overnight. Then 300 ml of chloroform was added and azeotrope containing water was removed until the head temperature reached 67°. Methanol (100 ml) was added and the reflux and azeotropic distillation with chloroform were repeated. Fractionation of the resultant product mixture gave 182.0 g (89%) of intermediate acyclic hemiketal, bp 50°–55° (0.50 mm). IR (neat): 2.9 (broad H-bonded OH), 3.33, 3.37, and 3.49 (sat'd CH), 5.62 (C=O), and 7.5–9.5μ (CF, C—O).

The intermedite acyclic hemiketal was added slowly to 142 g (1.0 mol) of P$_2$O$_5$; the resultant mixture was heated slowly and distilled to give 118.5 g (63% overall from lactol) of methyl perfluoro(2-methyl-5-oxo-3-oxahexanoate), bp 50° (50 mm). IR (CCl$_4$): 3.38 (weak sat'd CH), 5.58 with 5.61 sh (C=O), 7.5–9μ (CF, C—O). NMR: $^1$H 3.98 ppm (s, OCH$_3$); $^{19}$F −75.1 (t, $J_{FF}$ 6.1 Hz, 3F, CF$_3$C=O), −83.0 (d, $J_{FF}$ 3.2 Hz, 3F, CF$_3$), and −129.7 ppm (d of d of q, $J_{FF}$ 12.9, 9.7, 3.2 Hz, 1F, CF) with AB bands for CF$_2$ at −6693.2 and −6855.2 Hz (d of q, $J_{FF}$ 12.9, 6.1 Hz) and −7783.3 and −7806.5 Hz (d of q, $J_{FF}$ 9.7, 6.1 Hz). Anal Calc'd for C$_7$H$_3$F$_9$O$_4$: C, 26.10; H, 0.94; F, 53.09. Found: C, 25.81; H, 1.18; F, 53.17.

EXAMPLE 3

2-Oxo-6-(2,2,2-trifluoroethoxy)perfluoro(3,6-dimethyl-1,4-dioxane) and 2,2,2-Trifluoroethyl Perfluoro(2-methyl-5-oxo-3-oxahexanote)

This example demonstrates that treatment of the lactone perfluoro(3,6-dimethyl-2-oxo-1,4-dioxane) with an approximately equimolar amount of an alkanol, instead of excess alkanol as in Example 1, results in the formation of a (cyclic) lactone and an acyclic ketoester.

A suspension of 8.4 g (0.20 mol) of NaF in 31.4 g (0.10 mol) of the lactone perfluoro(2-oxo-3,6-dimethyl-1,4-dioxane) was stirred at 20° while 10.0 g (0.10 mol) of 2,2,2-trifluoroethanol was added. The resultant mixture was stirred overnight at 25°, after which analysis of the reaction mixture by infrared spectroscopy revealed the presence of lactone 2-oxo-6-[2,2,2-trifluoroethoxy]perfluoro(3,6-dimethyl-1,4-dioxane) (band at 5.47 $\mu$) and acyclic ketoester 2,2,2-trifluoroethyl perfluoro(2-methyl-5-oxo-3-oxahexanoate (band at 5.55$\mu$), along with some unreacted starting lactone (shoulder at 5.43$\mu$). The reaction mixture then was stirred at 100° for 6 h, after which time the infrared spectrum exhibited bands for the product lactone and ketoester only. Analysis of the mixture by $^1$H NMR showed the presence of about equal amounts of two types of —OCH$_2$CF$_3$, thus corresponding to a nearly equimolar mixture of product lactone and acyclic ketoester. The product components were found not to be separable by fractional distillation in a separate experiment.

EXAMPLE 4

Methyl Perfluoro(2,5-dimethyl-7-fluoroformyl-3,6-dioxaoctanoate)

A homogeneous mixture of 0.29 g (0.005 mol) of KF, 32.2 g (0.10 mol) of the ketoester methyl perfluoro(2-methyl-5-oxo-3-oxahexanoate and 50 ml of dry diglyme was stirred at 15° while 18.3 g (0.11 mol) of HFPO was distilled in batchwise over a 30-min period. The reaction mixture was stirred at 25° for 3 h; then, the pot was evacuated and heated to 50° (0.1 mm) to remove volatiles. Distillation of the volatiles so obtained, 46.6 g, gave 39.9 g (82%) of methyl perfluoro(2,5-dimethyl-7-fluoroformyl-3,6-dioxaoctanoate), bp 52.54° (10 mm). IR (CCl$_4$): 3.38 (weak sat'd CH), 5.31 (COF), 5.58 (C=O), 7.5–9$\mu$ (CF, C—O). NMR: $^1$H 3.98 ppm (s, OCH$_3$); $^{19}$F +26.3 (m, 1F, COF), −79.7 and −80.6 (m's 3F, CF$_3$), −83.2 (m, 3F, CF$_3$), −126.5 (m, 1F, CF), −132.6 (m, 1F, CF), and −144.4 ppm (m, 1F, CF), with two AB patterns for CF$_2$ with major branches (all broad m) at −7261.3, 7406.8, 7954.1, and −8096.9 Hz. Anal Calcd for C$_{10}$H$_3$F$_{15}$O$_5$: C, 24.61; H, 0.62; F, 58.39. Found: C, 24.95; H, 0.75; F, 58.65.

EXAMPLE 5

Methyl Perfluoro(2,5-dimethyl-3,6-dioxaoct-7-enoate)

A sample of the ester acid fluoride (34.0 g; 0.07 mol) from Example 4 was passed through a stirred bed of anhydrous Na$_3$PO$_4$ held at 257° (max.). The addition was carried out at 0.6 ml/min at one atm (101 kPa) with a slow N$_2$ purge. The liquid product was fractionated to afford 22.1 g (75%) of the vinyl ether methyl perfluoro(2,5-dimethyl-3,6-dioxaoct-7-enoate), bp 58°–60° (20 mm). IR showed a very weak band for COF at 5.3$\mu$ and NMR indicated the presence of a few % of starting material in addition to the vinyl ether. NMR: $^1$H 3.97 ppm (s, OCH$_3$); $^{19}$F −79.0 (broad A branches, 1F, C$\underline{F}$F), −80.5 (m, 3F, CF$_3$), −83.1 (m, 3F, CF$_3$), −85.0 (broad B branches, 1F, CF$\underline{F}$), −115 (2nd order m, 1F, =CF), −122 (2nd order, 1F, =CF), −132.3 (m, 1F, CF), −134 (2nd order m, 1F, =CF), −142.0 and −144.9 ppm (m, 1F combined, CF).

EXAMPLE 6

Perfluoro(4-methyl-3,6-dioxaocta-1,7-diene)

Pyrolysis of the ester acid fluoride of formula 2 over anhydrous Na$_2$CO$_3$ appears to be a more vigorous treatment than with Na$_2$PO$_4$ since both monovinyl and divinyl ethers were obtained, using the same starting material, under conditions similar to those of Example 5. Passage of 219 g (0.45 mol) of the ester acid fluoride over Na$_2$CO$_3$ at 260° in the stirred bed reactor of Example 5 was carried out at 0.6 ml/min at one atm (101 kPa) over a 3.5 h period. The crude product, which exhibited no substantial IR absorption for acid fluoride, was fractionated to give 91.2 g (48%) of the monovinyl ether methyl perfluoro(2,5-dimethyl-3,6-dioxaoct-7-enoate) and a considerable amount of lower boiler in the cold trap. For the monovinyl ether, IR (CCl$_4$): 3.32, 3.47, and 3.50 (sat'd CH), 5.58 (broad C=O, CF=CF$_2$), and 7.5–10$\mu$ (CF, C—O). Anal Calcd for C$_9$H$_3$F$_{13}$O$_4$: C, 25.61; H, 0.72; F, 58.51. Found: C, 25.74; H, 0.68; F, 58.57. The trap contents were fractionated to give 23.9 g (15%) of the divinyl ether perfluoro(4-methyl-3,6-dioxaocta-1,7-diene), bp 53°–55° (200 mm). NMR: $^{19}$F −80.5 (m, 3F, CF$_3$), −84.9 (m, 2F, CF$_2$), −136 (2nd order m, 2F, =CF), and −142.0 ppm (m, 1F, CF). Anal Calcd for C$_7$F$_{12}$O$_2$: C, 24.44; F, 66.26. Found: C, 24.35; F, 66.20.

EXAMPLE 7

Methyl Perfluoro(2,5-dimethyl-3,6-dioxanon-8-enoate)

A suspension of 5.80 g (0.10 mol) of oven-dried KF in 100 ml of diglyme was stirred at 0° while 32.2 g (0.10 mol) of methyl perfluoro(2-methyl-5-oxo-3-oxahexanoate) was added. A clear solution was obtained in about 15 min. Then there was added at 0°–5°, 23.0 g (0.10 mol) of CF$_2$=CFCF$_2$OSO$_2$F; the mixture was stirred at 5° for 2 h, then at 25° overnight, and then poured into 500 ml of water/50 ml CFCl$_2$CF$_2$Cl and shaken. The lower layer was washed with water, dried, and distilled to give 33.9 g of liquid, bp 49°–51° (10 mm), shown by IR and NMR to contain some diglyme. The distillate was dissolved in CFCl$_2$CF$_2$Cl and the resultant solution was extracted with 20 ml, then 10 ml of conc H$_2$SO$_4$, clarified with CaSO$_4$, filtered and distilled to give 22.0 g (47%) of product, bp 58°–59° (10 mm). IR (CCl$_4$): 5.59 (CO, CF=CF$_2$), 7.5–9.5$\mu$ (CF, C—O). NMR: $^1$H 3.97 ppm (s, OCH$_3$); $^{19}$F −69.5 (m, 2F, OCF$_2$C=), −80.8 (m, 3F, CF$_3$), −83.2 (d, J$_{FF}$ 2.9 Hz, 3F, CF$_3$), −92.9 (d of d of t of d, J$_{FF}$ 53.7, 39.5, 7.5, 1.3 Hz, 1F, cis—CF$_2$CF=C$\underline{F}$F), −105.7 (d of d of t, J$_{FF}$ 117.4, 53.7, 23.9 Hz, 1F, trans-CF$_2$CF=CF$\underline{F}$), −132.5 (m, 1F, CF), −146.8 (m, 1F, CF), and −190.7 ppm (d of d of t, J$_{FF}$ 117.4, 39.3, 13.9 Hz, 1F, CF$_2$C$\underline{F}$=CF$_2$), with broad AB multiplets for OC$\underline{F}$$_2$CF at −7375, −7525, −8057 and −8208 Hz. Anal Calcd for C$_{10}$H$_3$F$_{15}$O$_4$: C, 25.44; H, 0.64; F, 60.36. Found: C, 25.55; H, 0.69; F, 60.43.

EXAMPLE 8

Copolymerization of Methyl Perfluoro(2,5-dimethyl-3,6-dioxaoct-7-enoate) with Tetrafluoroethylene A mixture of 20 ml of $CFCl_2CF_2Cl$, 21.1 g (0.05 ml) of monovinyl ether which was prepared as in Example 5 or Example 6 and 0.2 ml of 5% perfluoropropionyl peroxide in $CFCl_2CF_2Cl$ was shaken at 45° in a 110-ml stainless steel-lined tube under 85 psi (586 kPa) of tetrafluoroethylene until uptake of tetrafluoroethylene had ceased (4 h). About 12 g of tetrafluoroethylene was consumed. The solid polymer produced was dried under vacuum, then stirred in a blender with a water-acetone mixture. Filtration and rinsing of the filter cake with methanol gave 7.1 g of copolymer after vacuum drying. A film pressed at 150° exhibited marked absorption in the infrared for ester $C=O$ (5.60μ).

A similar copolymerization carried out at 40° with 0.1 ml of catalyst solution resulted in the absorption of 8-9 g of tetrafluoroethylene. The polymer was worked up by drying under vacuum, extracting with $3 \times 100$ ml of methanol, then with acetone, then with a large volume of $CFCl_2CF_2Cl$, and finally drying under vacuum; 5.3 g of solid copolymer were recovered. A sample of this material was hydrolyzed on the steam bath with a $KOH/H_2O/DMSO$ (dimethylsulfoxide) mixture; the resultant product was rinsed well with $2 \times 75$ ml of hot $H_2O$, filtered and dried. The equivalent weight, as the potassium salt, was determined: 1310.

EXAMPLE 9

Copolymerization of Methyl Perfluoro(2,5-dimethyl-3,6-dioxanon-8-enoate) with Tetrafluoroethylene A mixture of 50 g (0.10 mol) of the allyl ether which was prepared as in Example 7 and 10 ml of 10% perfluoropropionyl peroxide in $CFCl_2CF_2Cl$ was shaken at 40° under 20 psi (138 kPa) of tetrafluoroethylene for 6 h. After 6 g of tetrafluoroethylene was consumed. The product was distilled to remove monomer and the resultant solid polymer was washed with $CFCl_2CF_2Cl$ and dried under vacuum; yield: 2.4 g. A sample was hydrolyzed as described in Example 8. The equivalent weight, as the potassium salt, was determined: 1360.

A 10 cm diameter film, pressed at 200°, was tested and utilized as a membrane in a chloroalkali electrolysis cell; the cell operated at 5.6 volts, 89% current efficiency and 32% sodium hydroxide concentration.

Best Mode For Carrying Out the Invention

The best mode for carrying out the invention is demonstrated by Examples 1, 4 and 5.

Industrial Applicability

The fluorinated ketoester 1 and its HFPO adduct 2 are useful as intermediates to the fluorinated vinyl ether 3, divinyl ether 4 and allyl ether 5. The vinyl, divinyl and allyl ethers are useful as copolymerizable monomers from which copolymers useful as molding resins can be prepared, selected species of the copolymers, after hydrolysis, being water-wettable and dyeable, exhibiting ion-exchange properties and being useful in curable fluoroelastomer compositions and, in film form, as the membrane in chloroalkali electrolysis cells.

Although the preferred embodiments of the invention have been illustrated and described, it is to be understood that there is no intention to limit the invention to the precise construction herein disclosed and it is to be further understood that the right is reserved to all changes and modifications coming within the scope of the invention as defined in the appended claims.

I claim:

1. Compound of the formula

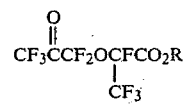

wherein R is alkyl of 1 to 8 carbon atoms.

2. Compound of claim 1 wherein R is alkyl of 1 to 4 carbon atoms.

3. Compound of claim 2 wherein R is methyl.

4. Process for preparing the compound of claim 1 by
   (a) contacting and reacting perfluoro(3,6-dimethyl-2-oxo-1,4-dioxane), 6, with a molar excess of alkanol ROH, wherein R is alkyl of 1 to 8 carbon atoms, at a temperature of 15°–150° C., to form the hemiketal, 9, of the formula

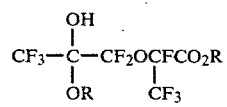

wherein R is as defined above; and
   (b) contacting and reacting, at a temperature of 15°–100° C., the hemiketal, 9, of step (a) with about 1 to 5 mols of phosphorus pentoxide per mol of hemiketal to form the compound of claim 1.

5. Process of claim 4 wherein step (a) is carried out in the presence of an alkali metal fluoride.

6. Process of claim 5 wherein the alkali metal fluoride is sodium fluoride.

7. Process of claim 4 wherein step (a) is carried out at 20°–50° C., and step (b) is carried out at 20°–40° C.

8. Process for preparing the compound of claim 1 by
   (a) contacting and reacting 2-oxo-6-hydroxyperfluoro(3,6-dimethyl-1,4-dioxane), 7, with a molar excess of alkanol ROH, wherein R is alkyl of 1 to 8 carbon atoms, at a temperature of 15°–150° C., to form the hemiketal, 9, of the formula

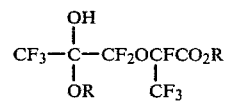

wherein R is as defined above; and
   (b) contacting and reacting, at a temperature of 15°–100° C., the hemiketal, 9, of step (a) with about 1 to 5 mols of phosphorus pentoxide per mol of hemiketal to form the compound of claim 1.

9. Process of claim 8 wherein step (a) is carried out in the presence of a strong acid.

10. Process of claim 9 wherein about 0.005 to about 0.05 mol of sulfuric acid is used.

11. Process of claim 9 wherein about 0.005 to about 0.05 mol of a sulfonic acid is used.

12. Process of claim 8 wherein step (a) is carried out at 20°–50° C., and step (b) is carried out at 20°–40° C.

13. Process for preparing the compound of claim 1 by
   (a) contacting and reacting 2-oxo-6-alkoxyperfluoro(3,6-dimethyl-1,4-dioxane), 8, wherein the alkoxy substituent has 1 to 8 carbon atoms, with a molar excess of alkanol ROH, wherein R is alkyl of 1 to 8 carbon atoms, at a temperature of 15°–150° C., to form the hemiketal, 9, of the formula

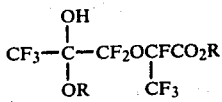

wherein R is as defined above, provided, however, the two R groups in the hemiketal formula can be the same or different; and (b) contacting and reacting, at a temperature of 15°–100° C., the hemiketal, 9, of step (a) with about 1 to 5 mols of phosphorus pentoxide per mol of hemiketal to form the compound of claim 1.

14. Process of claim 13 wherein the alkoxy substituent is methoxy.

15. Process of claim 13 wherein step (a) is carried out at 20°–50° C., and step (b) is carried out at 20°–40° C.

* * * * *